United States Patent
Kistner et al.

(10) Patent No.: US 8,382,680 B2
(45) Date of Patent: Feb. 26, 2013

(54) HAND-HELD INSTRUMENT FOR THE ANALYSIS OF BODY FLUIDS

(75) Inventors: Michael Kistner, Ludwigshafen (DE); Frank Deck, Niederkirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1132 days.

(21) Appl. No.: 11/472,020

(22) Filed: Jun. 21, 2006

(65) Prior Publication Data

US 2007/0004990 A1 Jan. 4, 2007

(30) Foreign Application Priority Data

Jun. 23, 2005 (EP) .................................. 05013559

(51) Int. Cl.
*A61B 5/00* (2006.01)
(52) U.S. Cl. ........ 600/583; 600/584; 606/181; 606/182
(58) Field of Classification Search .................. 600/583, 600/584; 606/181–183
See application file for complete search history.

(56) References Cited

U.S. PATENT DOCUMENTS

| | | | | |
|---|---|---|---|---|
| 4,539,988 | A * | 9/1985 | Shirley et al. ................ | 606/182 |
| RE32,922 | E | 5/1989 | Levin et al. | |
| 5,035,704 | A | 7/1991 | Lambert et al. | |
| 5,971,941 | A * | 10/1999 | Simons et al. ................ | 600/573 |
| 6,036,924 | A * | 3/2000 | Simons et al. ................ | 422/100 |
| 6,210,420 | B1 * | 4/2001 | Mauze et al. ................ | 606/182 |
| 6,315,738 | B1 | 11/2001 | Nishikawa et al. | |
| 6,493,592 | B1 * | 12/2002 | Leonard et al. .............. | 607/149 |
| 6,530,892 | B1 * | 3/2003 | Kelly ........................... | 600/583 |
| 6,589,260 | B1 * | 7/2003 | Schmelzeisen-Redeker et al. ............................. | 606/181 |
| 2002/0188224 | A1 * | 12/2002 | Roe et al. ..................... | 600/584 |
| 2004/0039303 | A1 * | 2/2004 | Wurster et al. ................ | 600/584 |
| 2004/0092996 | A1 * | 5/2004 | List et al. ...................... | 606/181 |
| 2004/0127819 | A1 * | 7/2004 | Roe ................................ | 600/583 |
| 2004/0230216 | A1 | 11/2004 | Levaughn et al. | |

(Continued)

FOREIGN PATENT DOCUMENTS

CA 2 532 441 A1 1/2005
DE 103 32 488 A1 2/2005

(Continued)

*Primary Examiner* — Rene Towa
(74) *Attorney, Agent, or Firm* — Bose McKinney & Evans LLP

(57) ABSTRACT

The present invention provides a hand-held analysis instrument for analyzing a body fluid. The instrument comprises a housing with a housing opening to which a body part, in particular, a finger, can be applied to generate a puncture wound, an analysis unit for analyzing a sample of a body fluid obtained at the puncture wound, and a piercing unit including a lancet and lancet drive for generating a puncture movement of the lancet. The piercing unit, including the lancet drive, is movable between an operating position and a rest position, the piercing unit being located at the housing opening in the operating position in such a manner that by means of the lancet a puncture wound can be generated in a body part pressed against the housing opening, and the piercing unit being remote from the housing opening in the rest position in such a manner that the space in front of the housing opening is free for the analysis unit, so that it can be moved into a position for receiving blood. An operating device is used for actuating a functional mechanism of the piercing unit. The piercing unit is decoupled from the operating device in one of its two positions and is coupled to the operating device in the other position.

25 Claims, 2 Drawing Sheets

U.S. PATENT DOCUMENTS

| | | | |
|---|---|---|---|
| 2004/0249406 A1* | 12/2004 | Griffin et al. | 606/182 |
| 2005/0011759 A1 | 1/2005 | Moerman et al. | |
| 2006/0155317 A1 | 7/2006 | List | |
| 2006/0173380 A1* | 8/2006 | Hoenes et al. | 600/583 |

FOREIGN PATENT DOCUMENTS

| | | |
|---|---|---|
| DE | 10 2004 059 491 A1 | 7/2006 |
| JP | 2000-217804 A | 8/2000 |
| JP | 2000217804 A * | 8/2000 |
| WO | WO 98/24366 | 6/1998 |
| WO | WO 02/078533 A2 | 10/2002 |
| WO | WO 03/071940 A1 | 9/2003 |
| WO | WO 2005/006985 A2 | 1/2005 |
| WO | WO 2005006985 A2 * | 1/2005 |

* cited by examiner

HAND-HELD INSTRUMENT FOR THE ANALYSIS OF BODY FLUIDS

RELATED APPLICATIONS

This application claims priority to European Patent Application No. EP 05 013 559.9, filed Jun. 23, 2005.

BACKGROUND

The present invention relates to a hand-held analysis instrument for analyzing a body fluid, and in particular, an instrument comprising a housing with a housing opening, a piercing unit for triggering a lancet to generate a puncture wound, an analysis unit for analyzing a body fluid obtained from a generated puncture wound, a transport unit for moving the piercing unit between an operating position, in which a puncture wound is generated, and a rest position, and an operating device for actuating a functional mechanism of the piercing unit. A hand-held analysis instrument of this type is known from DE 10332488 A1.

Depending on the depth of the puncture wound, the body fluid is interstitial fluid and/or blood. In the following description, blood is used as an example of the body fluid to be analyzed.

With hand-held analysis instruments containing (in addition to an analysis unit for analyzing blood) a piercing unit for generating a puncture wound, the blood sugar level can be measured far more easily than with analysis systems comprising a hand-held analysis instrument, a separate lancet device and test strips for the blood test.

In analysis systems with separate devices, a user must first generate a puncture wound by means of a lancet device, then apply the blood coming out of the wound to a test strip and finally insert this test strip into a hand-held analysis instrument for the actual measurement of blood glucose concentration.

Integrated hand-held analysis instruments of the above-mentioned type significantly simplify for the user the procedure of obtaining and measuring blood. It is sufficient to press the housing opening of the hand-held analysis instrument against a finger. By means of the piercing unit integrated in the device, a puncture wound is generated. Without intervention of the user, the issuing blood reaches the analysis unit where it is analyzed. The piercing unit for generating a puncture wound is first located in its operating position at the housing opening. Subsequently, it is moved by a transport unit into a rest position, so that the housing opening and the generated puncture wound are accessible to receive a sample.

Since diabetics must measure their blood sugar level several times a day and therefore continuously have to carry hand-held analysis instruments with them, there is a need to make the hand-held analysis instruments as small and compact as possible. In this context it is important to achieve low power consumption, since the output of internal power sources is limited. Frequent battery changes restrict the comfort of and inconvenience the user. Large batteries are not compatible with the requirement of a compact construction of the hand-held analysis instrument.

SUMMARY OF THE INVENTION

The present invention provides a hand-held analysis instrument of the above-mentioned type that can be manufactured more compactly and be operated with low energy consumption without restricting user comfort.

In one form thereof, the instrument comprises a housing, an analysis unit, a piercing unit, an operating device, and a transport unit. The piercing unit, including the lancet drive, is moved between an operating position and a rest position by the transport unit. In the operating position, the piercing unit is located close to the housing opening in such a manner that a puncture wound can be generated by the lancet in a body part pressed against the housing opening. In the rest position, the piercing unit is located sufficiently far from the housing opening that the space in front of the housing opening is free for the analysis unit, so that it can be moved into a position for receiving blood coming out of the body part pressed against the housing opening.

The piercing unit is decoupled from the operating device in one of its two positions and is coupled to the operating device in the other position, preferably being in mechanical engagement therewith.

The piercing unit of a hand-held analysis instrument typically has a plurality of functional mechanisms which are used for setting the piercing depth or for tensioning a drive spring. An operating device is required for each of these functional mechanisms, so that the corresponding functional mechanism can be actuated. The operating device has a corresponding operating element for the user, such as a rotary knob or a button.

In one embodiment, the piercing unit is coupled to the operating device in its rest position, for example, for tensioning a drive spring or setting the piercing depth, and decoupled from the operating device in its operating position. However, it is also possible for the piercing unit to be decoupled from the operating device in its rest position and to be operatively engaged with the operating device in the operating position.

The term "functional mechanism" comprises different mechanisms of the piercing unit, in particular, a tensioning mechanism for tensioning a drive spring of the lancet drive, a piercing depth setting mechanism for changing and adjusting the depth with which the lancet punctures the body part, and a position changing mechanism for advancing the lancet magazine into consecutive "firing positions", in which another lancet may engage with the lancet drive. The piercing unit has one or more of these functional mechanisms. The operation by the operating device can, in particular, be performed by a rotational movement or a translational movement. The functional mechanism can also be a triggering mechanism for triggering the pre-tensioned piercing unit, so that the lancet performs a puncture movement in order to puncture the body part pressed against the housing opening of the hand-held analysis instrument.

The power consumption of the hand-held analysis instrument can be reduced by the present invention, since only the piercing unit, and not the operating device, must be moved back and forth between the rest position and the operating position. The mass to be moved is thus reduced to a minimum, so that the power demand of the transport unit is correspondingly low. A further advantage is that the risk of failures is reduced because the functional mechanism is only actuated when it is coupled to the operating device. When the functional mechanism is decoupled from the operating device, incorrect actuation of the operating device has no effect on the functional mechanism.

The decoupling of the operating device from the piercing unit according to the present invention also allows a more compact construction of the hand-held analysis instrument. This is because a relatively small free space in the housing is sufficient, in which the piercing unit can be moved between operating position and the rest position. No additional free space is required for a corresponding movement of the operating device.

With the permanent coupling of the operating device to the piercing unit—as is common in the state of the art—mechanical operating elements, such as shafts movable by rotary knobs, must be guided through slots in the housing wall, so that they can be moved together with the piercing unit. Slots of this type have the disadvantage that dirt may reach the housing interior through them. Instead of maintaining the long-standing concept of a permanent coupling and avoiding disadvantageous slots, for example by electrical actuating elements connected by flexible wires to movable parts of the operating device, the present invention follows a new path by proposing an operating device which is coupled to or decoupled from the piercing unit depending on its position. In this way, the above-mentioned advantages of a more compact construction and a low power consumption can be achieved by a relatively simple mechanical construction.

As used herein, the statement that the piercing unit is decoupled from the operating device means that in this state no force transmission is possible from the operating device to the functional mechanism of the piercing unit. Preferably, there is also no contact between the operating device and the piercing unit in the decoupled state. A coupling can be performed electrically, for example, by closing an electrical contact. Preferably, however, the coupling is performed mechanically by operative engagement with the functional mechanism mechanically. If the operating device is operatively engaged with the piercing unit, a force can be mechanically transmitted from the operating device to the functional mechanism of the piercing unit. Preferably, a rotational movement, e.g. by means of shafts or gear wheels, is transmitted from the operating device to the functional mechanism to actuate the functional mechanism by operational engagement. This is possible by a frictional or—preferably—form-fitting coupling.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
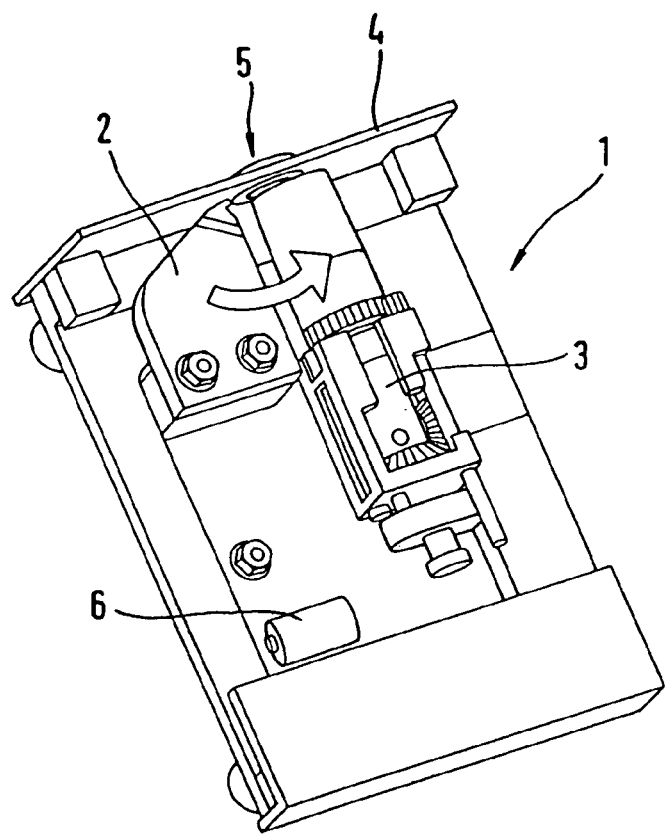
FIG. 1 is a perspective view of a hand-held analysis instrument with a housing shown partially removed.

FIG. 1 schematically shows an exemplary embodiment of a hand-held analysis instrument 1 having an analysis unit 2 for analyzing blood and a piercing unit 3 for generating a puncture wound. The piercing unit 3 includes a lancet (not shown) and a lancet drive (not shown) for triggering a puncture and retraction movement of the lancet. The hand-held analysis instrument 1 has a housing 4 with a housing opening 5, to which a body part, such as a finger, is applied to generate a puncture wound.

If the piercing unit 3 is in the operating position, as shown in FIG. 1, a puncture wound can be generated in a body part pressed against the housing opening 5. After the puncture, the piercing unit 3 is moved by a transport unit (not shown) by a pivot or translational movement to a rest position. The analysis unit 2 is moved into the space vacated by the piercing unit 3 so that the analysis unit 2 reaches a position for collecting blood from the generated puncture wound.

In the exemplary embodiment shown, the analysis unit 2 contains a cassette including a band-shaped test strip. The test strip has a plurality of band sections coated with chemicals which react with collected blood and cause a visually detectable color change corresponding to the blood sugar concentration. The analysis unit 2 and other electrical components of the hand-held analysis instrument 1 are supplied with power by an internal power source 6 such as, for example, a battery.

In FIG. 1, no operating devices for actuating functional mechanisms of the piercing unit 3 are shown. These operating devices and functional mechanisms of the piercing unit 3 are shown in and described with reference to FIGS. 2 and 3.

Figure 2:
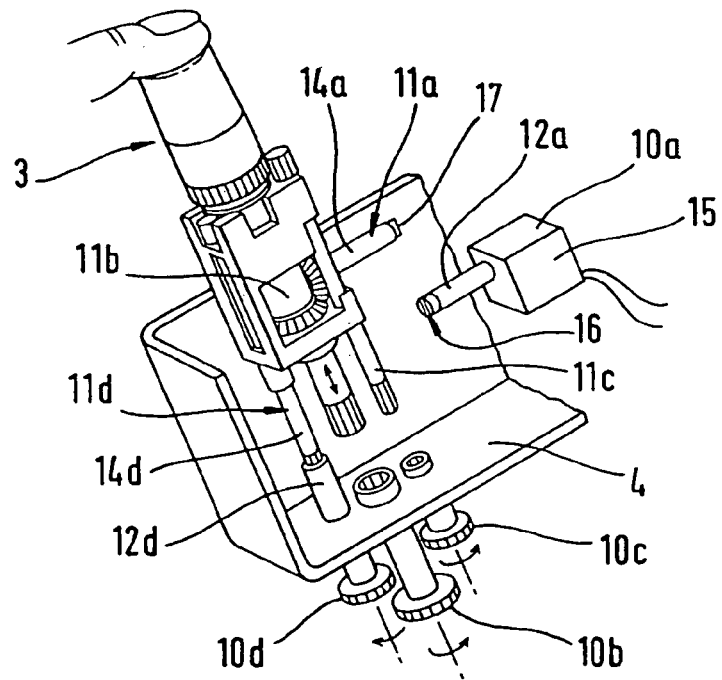
FIG. 2 is a partial perspective view of the hand-held analysis instrument shown in FIG. 1, in which the piercing unit is shown in the operating position.
Figure 3:
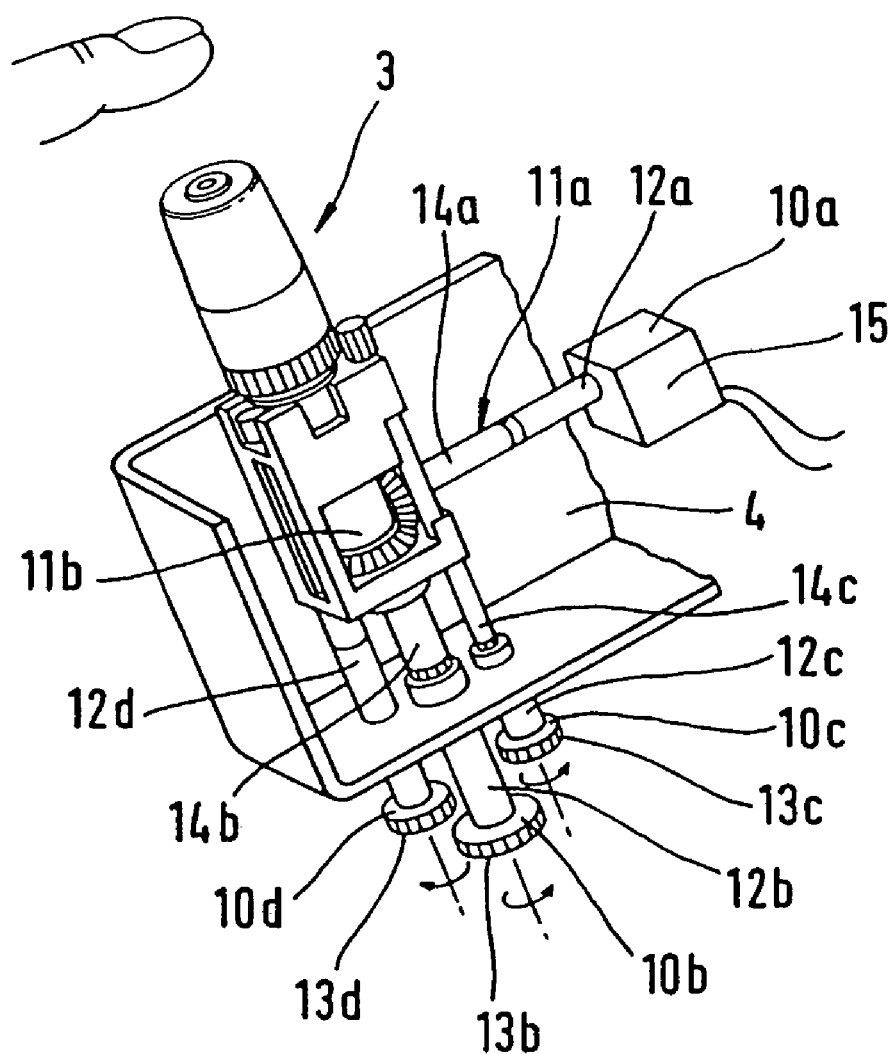
FIG. 3 is a partial perspective view of the hand-held analysis instrument shown in FIG. 1, in which the piercing unit is shown in the rest position.

FIG. 2 shows the piercing unit 3 in the operating position. In contrast, FIG. 3 shows the piercing unit 3 in the rest position. The piercing unit 3 moves back and forth between these two positions. The analysis unit 2 is moved from a position remote from the housing opening 5, as shown in FIG. 1, to an analysis position. In the analysis position, the analysis unit 2 is positioned sufficiently close to the housing opening 5 to collect and analyze fluid protruding from a punctured wound of a body part. In this analysis position, the analysis unit 2 is moved to a similar position at the housing opening 5 taken by the piercing unit 3 when it is in an operating position. The analysis unit 2 and the piercing unit 3 are thus alternately moved into direct proximity to the housing opening 5.

FIG. 2 shows the piercing unit 3 in the operating position together with a plurality of operating devices 10a, 10b, 10c, 10d, which are used for actuating functional mechanisms 11a, 11b, 11c, 11d of the piercing unit 3. As shown in FIG. 2, the piercing unit 3 has a first functional mechanism 11a for tensioning a drive spring, a second functional mechanism 11c for setting the piercing depth, a third functional mechanism 11b for rotating a lancet magazine mounted in the piercing unit 3, and a fourth functional mechanism 11d for triggering a puncture and retraction movement of a lancet.

A piercing unit having such functional mechanisms is known in the art and is described, for example, in German Patent Application 102004059491.0, which is hereby incorporated by reference in its entirety.

When the piercing unit 3 is in the operating position, as shown in FIG. 2, only operating device 10d is operatively engaged with the piercing unit 3, or more precisely, to the functional mechanism 11d. The other operating devices 10a, 10b, 10c are decoupled from the piercing unit 3, or more precisely, from the associated functional mechanisms 11a, 11b, and 11c, respectively. In FIG. 3, the piercing unit 3 is shown in its rest position. In the rest position, operating devices 10a, 10b, and 10c are operatively engaged with the piercing unit 3, while operating device 10d is decoupled from the piercing unit 3.

The operational engagement of the piercing unit 3 with operating devices 10a, 10b, 10c, 10d is used for transmitting rotational movements from the particular operating device 10a, 10b, 10c, 10d to the associated functional mechanism 11a, 11b, 11c, 11d of the piercing unit 3. For this purpose, each operating device 10a, 10b, 10c, 10d comprises a shaft 12a, 12b, 12c, and 12d, respectively, which can be coupled in a formfitting way to the particular functional mechanism 11a, 11b, 11c, and 11d, respectively, of the piercing unit 3.

The operating device 10d comprises a shaft 12d projecting through the outer wall of the housing 4, which has a rotary knob 13d on its end projecting out of the housing 4. The shaft 12d is designed as a hollow shaft, so that it can be pushed onto a fitting shaft 14d (FIG. 2) of functional mechanism 11d, which triggers the piercing unit 3. The two shafts 12d and 14d are connected by a spline connection in the operating position of the piercing unit 3 shown in FIG. 2. The spline bore hubs are only provided in a front section of the shaft 12d. The internal diameter of the shaft 12d slightly increases behind the section with the spline bore hubs, so that in the rest position of the piercing unit 3 shown in FIG. 3, no rotational movement can be transmitted from shaft 12d to shaft 14d. The operating device 10d is thus decoupled from the functional mechanism 11d.

The construction of the operating devices 10b and 10c corresponds to the construction of the operating device 10d. The operating devices 10b and 10c each comprise a shaft 12b or 12c, respectively, projecting through an outer wall of the housing 4. On the end of the shafts 12b or 12c, respectively, a rotary knob 13b or 13c, respectively, is attached which is accessible to a user. The shafts 12b and 12c are operatively engaged by a spline connection with corresponding shafts 14b and 14c, respectively, of the functional mechanisms 11b and 11c, respectively, while the piercing unit 3 is in the rest position shown in FIG. 3. Instead of a spline connection, other formfitting connections, such as serrations or polygonal profiles, can be used for coupling shafts 12b and 14b or 12c and 14c.

The operating device 10a comprises an electric motor 15 for actuating the functional mechanism 11a to tension a drive spring of the piercing unit 3. The motor 15 drives a shaft 12a, which is coupled to the shaft 14a of the functional mechanism 11a in the rest position of the piercing unit 3 shown in FIG. 3. The operating device 10a also comprises an operating element (not shown) in form of a button, for example, for switching on the electric motor.

In contrast to the shafts 12b, 12c and 12d, the shaft 12a runs transversely to the direction in which the piercing unit 3 is shifted during its movement from the rest position to the operating position. The shaft 12a therefore has a slot 16 on its end facing away from the motor 15. When the piercing unit 3 is in the rest position, a web 17 on the free end of the shaft 14a engages with the slot 16 according to the principle of a tongue and groove connection.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS 1 hand-held analysis instrument
2 analysis unit
3 piercing unit
4 housing
5 housing opening
6 power source
10a-d operating device
11a-d functional mechanism
12a-d shaft (of operating device)
13b-d rotary knob
14a-d shaft (of functional mechanism)
15 motor
16 slot
17 web

What is claimed is:

1. A hand-held instrument for analyzing a body fluid, comprising:
    a housing having a housing opening to which a body part can be applied to generate a puncture wound;
    an analysis unit for analyzing a sample of a body fluid obtained at the puncture wound;
    a piercing unit disposed in the housing and including a lancet and a lancet drive for driving a puncture movement of the lancet;
    a transport unit for moving the piercing unit, including the lancet and lancet drive, relative to the housing between an operating position and a rest position, the piercing unit in the operating position being located at the housing opening such that a puncture wound can be generated by the lancet in the body part when the body part is pressed against the housing opening, the piercing unit being remote from the housing opening in the rest position, wherein the analysis unit can be moved relative to the housing into a position for receiving body fluid when the body part is pressed against the housing opening when the piercing unit is in the rest position;
    a functional mechanism connected to the piercing unit, the functional mechanism moving with the piercing unit between the operating position and the rest position; and
    an operating device for actuating the functional mechanism, wherein the piercing unit is movable relative to the operating device, the piercing unit being decoupled from the operating device in one of the operating position and the rest position and being coupled to the operating device in the other one of the operating position and the rest position.

2. The hand-held instrument of claim 1, wherein
    when the operating device is decoupled from the piercing unit, no force transmission is possible from the operating device to the functional mechanism of the piercing unit, and
    when the operating device is coupled to the piercing unit, a force can be transmitted from the operating device to the functional mechanism.

3. The hand-held instrument of claim 1, wherein the piercing unit is moved between its rest position and its operating position by a pivot movement or a translational movement.

4. The hand-held instrument of claim 1, wherein the analysis unit comprises a cassette including a band-shaped test strip.

5. The hand-held instrument of claim 1, wherein the functional mechanism is a tensioning mechanism for tensioning a drive spring, a piercing depth setting mechanism, a position changing mechanism for a magazine, or a trigger mechanism for triggering a puncture movement of a lancet.

6. The hand-held instrument of claim 1, wherein the piercing unit is decoupled from the operating device in the operating position and is operatively engaged with the operating device in the rest position.

7. The hand-held instrument of claim 1, wherein the operational engagement of the piercing unit with the operating device transmits a rotational movement from the operating device to the functional mechanism of the piercing unit.

8. The hand-held instrument of claim 1, wherein the operating device comprises a shaft.

9. The hand-held instrument of claim 8, wherein the shaft projects through an outer wall of the housing.

10. The hand-held instrument of claim 1, wherein the operational engagement of the piercing unit with the operating device is formfitting.

11. The hand-held instrument of claim 1, wherein the piercing unit comprises a drive rotor driven by a drive spring.

12. The hand-held instrument of claim 1, wherein the operating device comprises a motor located in the housing for tensioning the drive spring.

13. The hand-held instrument of claim 1, wherein the piercing unit comprises a receptacle for a lancet magazine including a plurality of lancets which are movable in sequence into a coupling position in which they can be coupled to the lancet drive by rotating the lancet magazine, the functional mechanism of the piercing unit being actuatable by the operating device and being used for rotating the lancet magazine.

14. The hand-held instrument of claim 1, wherein the operating device comprises a plurality of operating devices with which the piercing unit is operatively engaged in one of the operating and rest positions and from which the piercing unit is decoupled in the other of the operating and rest positions.

15. A hand-held instrument for analyzing a body fluid, comprising:
a housing having an opening;
an analysis unit for analyzing a body fluid sample;
a piercing unit disposed in the housing and including a lancet drive for triggering a puncture and retraction movement of a lancet, the piercing unit, including the lancet and lancet drive, being moveable in the housing between an operating position and a rest position;
a functional mechanism connected to the piercing unit, the functional mechanism moving with the piercing unit between the operating position and the rest position; and
an operating device for actuating the functional mechanism, wherein the piercing unit is movable relative to the operating device, the piercing unit being decoupled from the operating device in one of the operating position and the rest position and being coupled to the operating device in the other one of the operating position and the rest position;
wherein, the analysis unit and piercing unit are alternatively movable into direct proximity to the opening.

16. The hand-held instrument of claim 15, wherein in the operating position the piercing unit is positioned close to the opening and in the rest position the piercing unit is positioned remote from the opening.

17. The hand-held instrument of claim 15, wherein the piercing unit is moved between its rest position and its operating position by a pivot movement or a translational movement.

18. The hand-held instrument of claim 15, further comprising an analysis unit disposed in the housing.

19. The hand-held instrument of claim 15, wherein the functional mechanism comprises a tensioning mechanism for tensioning a drive spring, a piercing depth setting mechanism, a position changing mechanism for a magazine, or a trigger mechanism for triggering a puncture movement of a lancet.

20. The hand-held instrument of claim 15, wherein the operational engagement of the piercing unit with the operating device transmits a rotational movement from the operating device to the functional mechanism of the piercing unit.

21. The hand-held instrument of claim 15, wherein the piercing unit comprises a drive rotor driven by a drive spring.

22. The hand-held instrument of claim 15, wherein the piercing unit comprises a receptacle for a lancet magazine.

23. The hand-held instrument of claim 15, wherein the operating device comprises first and second operating devices for actuating first and second functional mechanisms of the piercing unit, the first operating device being coupled to the first functional mechanism and the second operating device being decoupled from the second functional mechanism when the piercing unit is in the operating position.

24. The hand-held instrument of claim 23, wherein the first operating device comprises a trigger mechanism for triggering a puncture movement of a lancet.

25. The hand-held instrument of claim 23, wherein the second operating device comprises a tensioning mechanism for tensioning a drive spring, a piercing depth setting mechanism, or a position changing mechanism for a magazine drive spring.

* * * * *